US00PP11147P

United States Patent [19]

Kordes

[11] Patent Number: Plant 11,147

[45] Date of Patent: Dec. 7, 1999

[54] MINIATURE ROSE PLANT NAMED 'KORSAILER'

[75] Inventor: Wilhelm Kordes, Sparrieshoop, Germany

[73] Assignee: Bear Creek Gardens, Inc., Medford, Oreg.

[21] Appl. No.: 09/046,372

[22] Filed: Mar. 23, 1998

[51] Int. Cl.[6] ..... A01H 5/00

[52] U.S. Cl. ..... Plt./117

[58] Field of Search ..... Plt./117, 124

*Primary Examiner*—Howard J. Locker

*Attorney, Agent, or Firm*—Klarquist Sparkman Campbell Leigh & Whinston, L.L.P.

[57] ABSTRACT

Miniature rose plant having clear white flower color; compact but vigorous growth habit; ability to root easily from softwood cuttings; ability to flower quickly from cuttings; and a long shelf life.

1 Drawing Sheet

The present invention relates to a new and distinct variety of rose plant of the miniature class which was originated by me by crossing an unnamed seedling with an unnamed seedling.

The primary objective of this breeding was to produce a new miniature rose variety having clear white flower color; compact but vigorous growth habit; long shelf life; ability to root easily from softwood cuttings; ability to flower quickly from cuttings; and a long shelf life. The objective was substantially achieved, along with other desirable improvements, as evidenced by the following unique combination of characteristics that are outstanding in the new variety and that distinguish it from its parents, as well as from all other varieties of which I am aware:

1. Compact but vigorous growth habit;
2. Clear white flower color;
3. Ability to root quickly from softwood cuttings;
4. Long shelf life;
5. Flowers quickly.

'KORsailer' was bred, selected, and tested as a 4" (10 cm) pot rose. Its good shelf life, compact vigorous growth, and ease of growing make it an excellent pot rose for greenhouse production and mass merchant sales. Shelf life after four days shipping is at least eighteen days.

Asexual reproduction of this new variety by cutting propagation, as performed at Sparrieshoop, Germany, and Wasco and Somis, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

In such illustration, the blooms shown along the right side are blooms as viewed from above in the following stages starting with the lowermost bloom:

Bloom on day one starting to open;
Bloom on day two;
Bloom on day three;
Bloom on day four;
Bloom on day seven or eight.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling, not patented.

*Pollen parent.*—Unnamed seedling, not patented.

Classification:

*Botanical.*—Rosa hybrida.

*Commercial.*—Miniature rose.

FLOWER

Observations made from specimens grown in a greenhouse environment at Sparrieshoop, Germany and at Somis, Calif. from January, 1996 to December, 1997.

Blooming habit: Continuous.

Bud:

*Size.*—Five-eights inch when the petals start to unfurl.

*Form.*—The bud form is short, pointed ovoid.

*Color.*—When sepals first divide, bud color is Green-White Group 157D. When half blown, the upper sides of the petals are White Group 155D and the lower sides of the petals are White Group 155D.

*Sepals.*—Color: Green group 138A. Surface texture: Covered in fine hairs. There are three lightly to normally appendaged sepals. There are two unappendaged sepals with hairy edges.

*Receptacle.*—Color: Yellow-Green Group 137B. Shape: Funnel. Size: Small (7/32"×3/16"). Surface: Smooth.

*Peduncle.*—Length: Short (3/4" to 1"). Surface: Glandular. Color: Yellow-Green Group 146C. Strength: Stiff, erect.

Bloom:

*Size.*—Small. Average open size is 1 3/4 inches.

*Borne.*—Singly, several together in clusters of three to five flowers having a pyramidal, flat shape.

*Stems.*—Short, normal. Average length is about five inches.

*Form.*—When first open: High centered. Permanence: Flattens, all petals curl quill fashion.

*Petalage.*—Number of petals under normal conditions: 55–60.

*Color.*—The upper sides of the petals are White Group 155D. The reverse sides of the petals are White Group 155D. The base of each petal has a small (3/32"×3/32"), Yellow-Green Group 145C, half moon at the point of attachment. The major color on the upper sides is White Group 155D.

*Variegations.*—Occasional greenish streak on the guard petals.

*Discoloration.*—The flowers last on the plant without color change until petal drop at day 10 or 11.

*Fragrance.*—None.

Petals:

*Texture.*—Medium.

*Shape.*—Deltoid.

*Form.*—Tips slightly recurved, edges slightly quilled.

*Arrangement.*—Imbricated. Petaloids in the center are many and small.

*Persistence.*—Petals drop off cleanly before drying.

*Lastingness.*—On the plant: Very long (10 days). As a cut flower: Long (12–13 days).

Reproductive parts:

*Anthers.*—Size: Small. Quantity: Few. Color: Yellow. Arrangement: Regular around styles.

*Filaments.*—Color: Greenish-White.

*Pollen.*—Color: Lemon yellow.

*Styles.*—Color: Greenish-White.

*Stigmas.*—Color: Greenish-White.

Plant:

*Form.*—Bush.

*Growth.*—Vigorous; dwarf; upright; branching. At maturity, height is eighteen inches, width is twelve inches in a garden setting in Somis, Calif. When grown in a 4"×3" pot, the plant is seven inches in height and six to seven inches wide.

Foliage: Number of leaflets on normal mid-stem leaves: Five.

*Size.*—Small (2⅜" long×1¾" wide).

*Quantity.*—Abundant.

*Color.*—New foliage: Upper and lower surfaces: Greyed-Orange Group 173B, but quickly turn green colors of the mature leaf. Old foliage: Upper surface: Green Group 139A. Lower surface: Green Group 139C.

*Shape.*—Pointed oval.

*Texture.*—Upper side: Leathery, glossy.

*Edge.*—Serrated.

*Serration.*—Single, small.

*Petiole Rachis.*—Color: Yellow-Green Group 146C.

*Petiole Underside.*—Smooth with occasional prickles.

*Stipules.*—Short (5/16"), serrated, bearded.

*Disease Resistance.*—Resistant to mildew under normal growing conditions at Sparrieshoop, Germany and Somis, Calif.

Wood:

*New wood.*—Color: Green Group 137D. Bark: Smooth.

*Old wood.*—Color: Green Group 137C. Bark: Smooth.

Prickles:

*Quantity.*—On main canes from base: Ordinary. On laterals from main canes: Ordinary.

*Form.*—Short, straight.

*Color when young.*—Red.

Small prickles:

*Quantity.*—On main stalks: None. On laterals: None.

I claim:

1. A new and distinct variety of miniature rose plant as herein shown and described characterized particularly by its clear white flower color; compact but vigorous growth habit; ability to root easily from softwood cuttings; ability to flower quickly from cuttings; and a long shelf life.

* * * * *

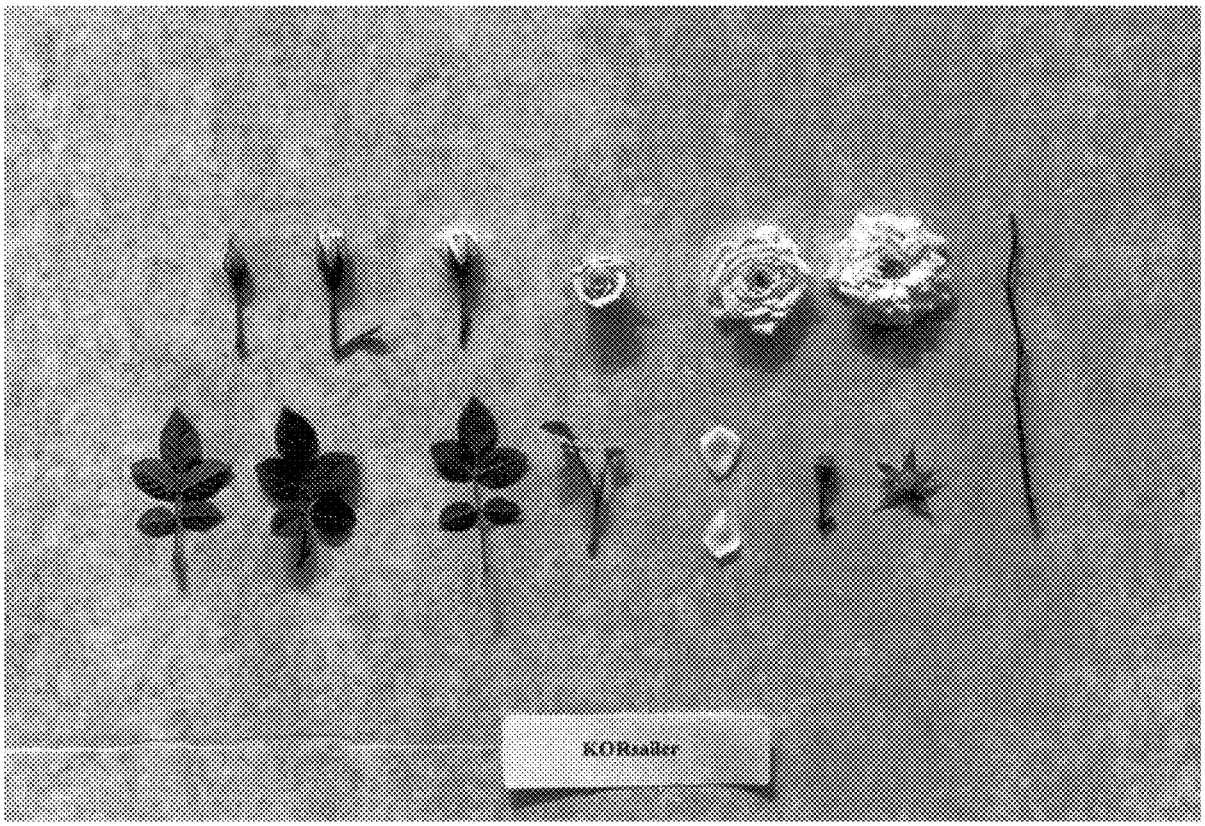
K.O.Raller